United States Patent [19]
Parsonnet

[11] Patent Number: 4,541,440
[45] Date of Patent: Sep. 17, 1985

[54] BIPOLAR EPICARDIAL TEMPORARY PACING LEAD

[75] Inventor: Victor Parsonnet, Millburn, N.J.

[73] Assignee: Cordis Corporation, Miami, Fla.

[21] Appl. No.: 671,290

[22] Filed: Nov. 14, 1984

[51] Int. Cl.⁴ .............................................. A61N 1/04
[52] U.S. Cl. ................................. 128/785; 128/419 P
[58] Field of Search ..................... 128/419 P, 784, 785

[56] References Cited

U.S. PATENT DOCUMENTS

| | | | |
|---|---|---|---|
| 3,244,174 | 4/1966 | Wesbey et al. | 128/418 |
| 3,333,045 | 7/1967 | Fisher et al. | 174/20 |
| 3,474,791 | 10/1969 | Bentov | 128/418 |
| 4,144,889 | 3/1979 | Tyers et al. | 128/418 |
| 4,338,947 | 7/1982 | Williams | 128/642 |
| 4,442,840 | 4/1984 | Wojciechowicz, Jr. | 128/419 P |
| 4,444,207 | 4/1984 | Robicsek | 128/785 |

*Primary Examiner*—W. E. Kamm
*Attorney, Agent, or Firm*—Henry W. Collins; Thomas R. Vigil

[57] ABSTRACT

The bipolar epicardial temporary pacing lead (10 or 110) comprises a lead body (22 or 122) containing first and second spaced apart wire conductors (24 or 124 and 26 or 126) each encased in insulating material (30 or 130) so as to form first and second insulated wire conductor portions (32 or 124 and 33 or 136). A straight needle (16 or 116) is connected to the proximal end portion (12 or 112) of the lead body (22 or 122). A curved needle (62 or 162) is connected to at least one of the wire conductors (24 or 124) at the distal end portion (14 or 114) of the lead (10 or 110). The distal end portion (14 or 114) of the lead (10 or 110) has insulation removed from portions of the respective first and second conductors (24 or 124 and 26 or 126) thereby to form in the distal end portion (14 or 114) a first or proximal electrode forming wire conductor portion (54 or 154) and a second or distal electrode forming or wire conductor portion (56 or 156). Terminal connector sleeves (34 and 36) are fixed on and around each insulated wire conductor portion (32 or 134 and 33 or 136) in the proximal end portion (12 or 112) of the lead (10 or 110) and in electrical contact with the wire conductor (24 or 124 and 26 or 126) therein.

28 Claims, 7 Drawing Figures

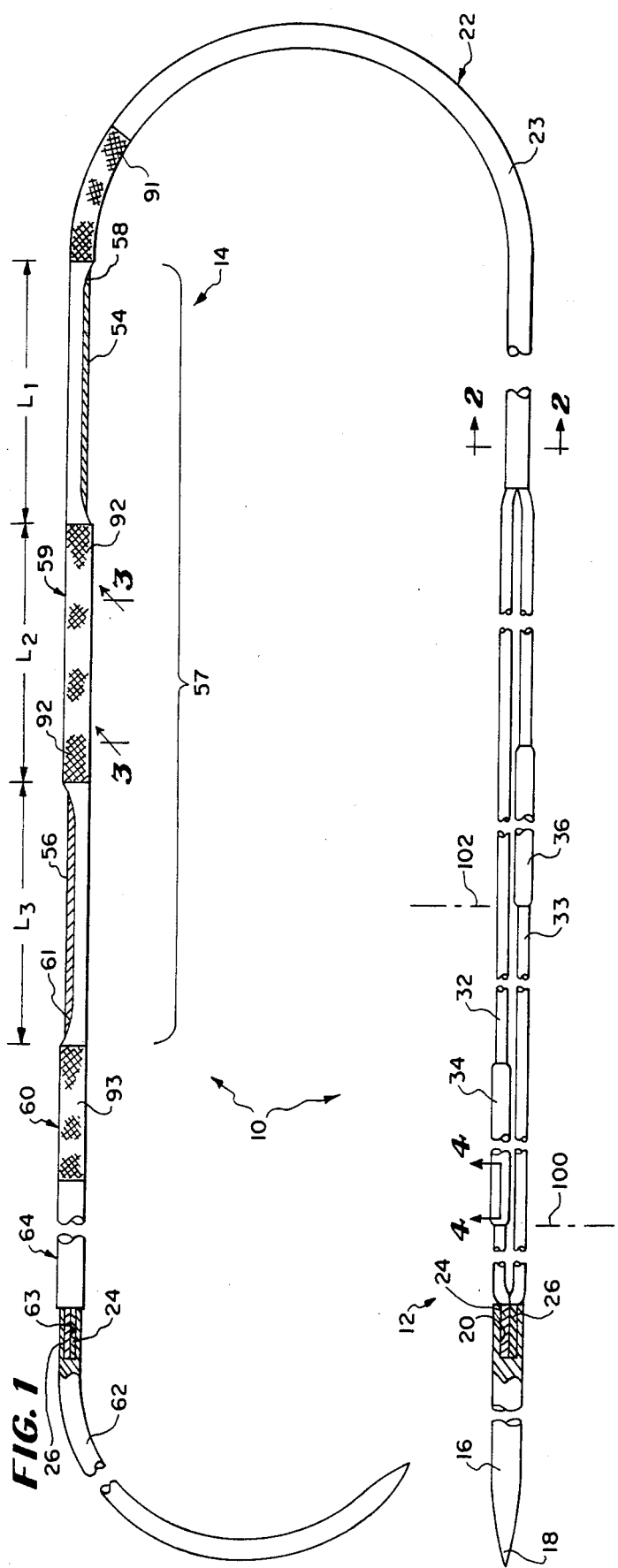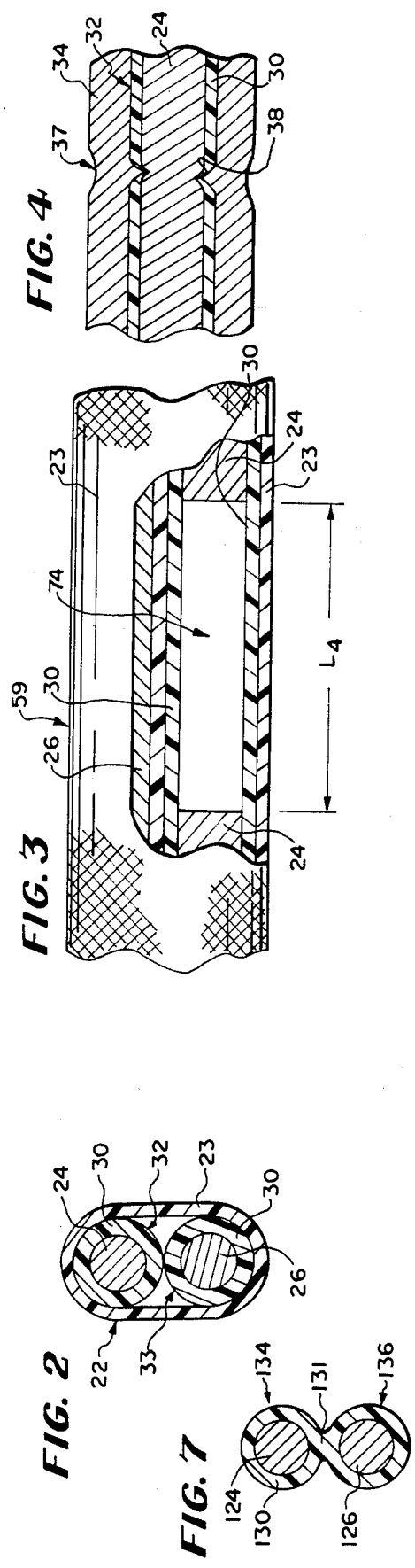

BIPOLAR EPICARDIAL TEMPORARY PACING LEAD

BACKGROUND OF THE INVENTION

1. Field of the Invention

The present invention relates to a device which is temporarily anchored within heart tissue for applying electrical stimuli to the heart. More specifically, the present invention is directed to a bipolar epicardial temporary pacing lead.

2. Description of the Prior Art

Heretofore various devices have been proposed for fixing a pacing lead to heart tissue by making an incision through the chest wall and then implanting an electrode within the myocardium of the heart wall. Examples of such previously proposed body implantable electrodes are disclosed in the following U.S. Patents:

| U.S. PAT. NO. | PATENTEE |
| --- | --- |
| 3,244,174 | Wesbey et al |
| 3,333,045 | Fisher et al |
| 3,474,791 | Bentov |
| 4,144,889 | Tyers et al |
| 4,338,947 | Williams et al |
| 4,442,840 | Wojciechowicz, Jr. |
| 4,444,207 | Robicsek |

All the prior temporary electrode devices (i.e., temporary pacing leads) have utilized single conductors with each conductor having a curved needle at the end thereof for insertion into (for threading the electrode through) heart tissue such as the epicardium to implant an exposed portion of the lead (electrode) within the myocardium of the heart. Often it is desired to place two such electrodes in the heart to provide for bipolar pacing.

In this respect, it is common to supply an electrical signal from a pulse generator in a pacer through one wire conductor to an electrode fixed to the myocardium so that the signal can pass through the myocardium causing the heart muscle to be depolarized and contract and then return by a second electrode also fixed to the myocardium and its wire conductor to the pacer having the pulse generator therein.

As will be described in greater detail hereinafter, the bipolar epicardial temporary pacing lead of the present invention differs from the previously proposed temporary pacing leads by providing a bipolar epicardial temporary pacing lead which has only one distal curved needle and one proximal percutaneous needle while at the same time providing two (bipolar) electrodes. Such bipolar epicardial temporary pacing lead requires only one puncture site at each end, thereby minimizing trauma to the heart and body wall.

SUMMARY OF THE INVENTION

According to the invention there is provided a bipolar temporary pacing lead comprising a lead body having a proximal end portion and a distal end portion and including first and second spaced apart wire conductors each encased in insulating material to form insulated wire conductors. A curved needle is connected to at least one of the first and second wire conductors in the lead body distal end portion. A straight needle is connected to the proximal end portion of the lead body. The distal end portion of the lead body has insulation removed from portions of the respective first and second conductors thereby to form in the lead body distal end portion, a first electrode-forming bare wire conductor portion and a second electrode-forming bare wire conductor portion.

Further according to the invention there is provided a bipolar epicardial temporary pacing lead comprising a lead body having a proximal end and a distal end and including first and second spaced apart wire conductors each encased in insulating material so as to form first and second insulated wire conductor portions and a sheath in which the insulated wire conductor portions are received. A straight needle is connected to the proximal end of said lead body. A curved needle is connected to the distal ends of the first and second wire conductors. The distal end portion of the lead body has portions of the sheath removed therefrom and adjacent portions of the respective first and second conductors thereby to form in the lead body distal end portion a proximal first electrode-forming wire conductor portion and a distal or second electrode-forming wire conductor portion.

Still further according to the invention there is provided a method for implanting a bipolar temporary pacing lead comprising a lead body having a proximal end portion and a distal end portion and including first and second spaced apart wire conductors each encased in insulating material to form insulated wire conductors. A curved needle is connected to at least one of the first and second wire conductors in the lead body distal end portion. A straight needle is connected to the proximal end portion of the lead body. The distal end portion of the lead body has insulation removed from portions of the respective first and second conductors thereby to form in the lead body distal end portion a first electrode-forming, bare wire conductor portion and a second electrode-forming bare wire conductor portion. The first electrode-forming wire conductor portion being proximal to and spaced from the second electrode-forming bare wire conductor portion such that the first electrode is a proximal electrode and the second electrode is a distal electrode. A first terminal connector sleeve is fixed around the first insulated wire conductor portion and electrically and mechanically connected to the first wire conductor therein and a second terminal connector sleeve spaced from the first terminal sleeve connector is fixed around the second insulated wire conductor portion and electrically and mechanically connected to the second wire conductor therein in the proximal end portion of the lead body in an exposed heart.

The method includes the steps of:

taking a first bite with the curved needle through the epicardium to place the proximal electrode in the myocardium;

taking a second bite with the curved needle through the epicardium to place the distal electrode in the myocardium spaced from the proximal electrode;

temporarily connecting a pulse generator to the terminal connector sleeves and electrically checking the functioning of the electrodes and if they function properly, disconnecting the pulse generator;

cutting off wire conductor end portion(s) close to the epicardium;

passing the straight needle through a puncture site in a patient's chest wall;

leaving a portion of the lead body in the chest cavity to compensate for heart contractions and body movement;

placing appropriate identification tags over the connector sleeves;

cutting the respective wire conductor portions flush with the proximal ends of the respective terminal connector sleeves; and inserting the terminal connector sleeves in respective female sockets therefor in a pacer.

BRIEF DESCRIPTION OF THE DRAWINGS

FIG. 1 is a plan view of one preferred embodiment of the bipolar epicardial temporary pacing lead of the present invention including a lead body with a curved needle at the distal end thereof and a straight needle at the proximal end thereof.

FIG. 2 is a sectional view of the lead body showing a cross-section of a sheath enclosing two insulated wire conductors and is taken along line 2—2 of FIG. 1.

FIG. 3 is an enlarged fragmentary partially sectional view of the lead body showing a gap in one of the conductors in the lead body and is taken along line 3—3 of FIG. 1.

FIG. 4 is a fragmentary sectional view of a connector sleeve received about one of the insulated wire conductors at the proximal end of the pacing lead shown in FIG. 1 and is taken along line 4—4 of FIG. 1.

FIG. 7 is a sectional view of the lead body of the pacing lead shown in FIG. 6 and is taken along line 7—7 of FIG. 6.

DESCRIPTION OF THE PREFERRED EMBODIMENTS

Figure 5:
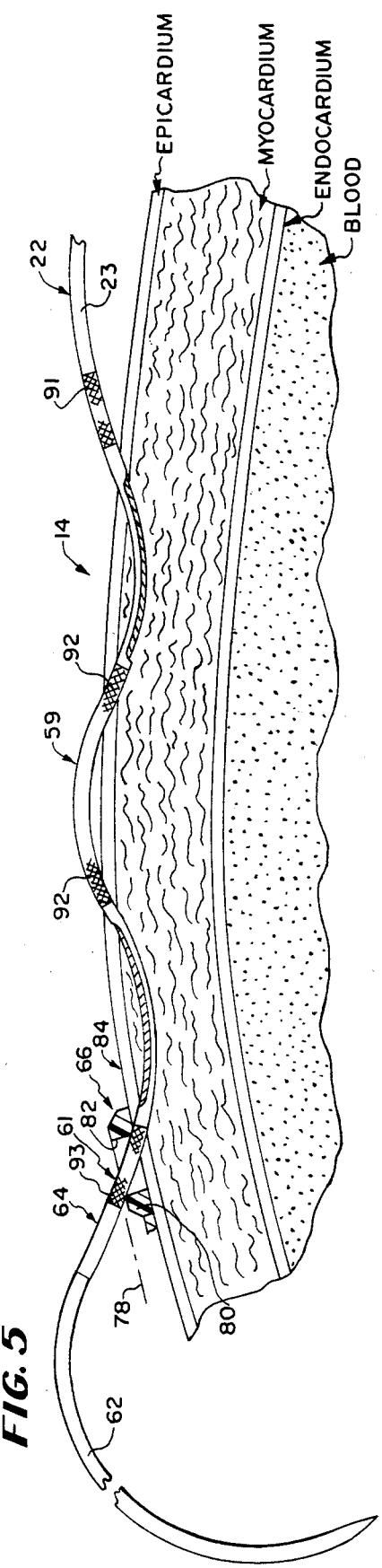
FIG. 5 is a fragmentary sectional view of a portion of heart tissue and shows the distal end of the bipolar epicardial temporary pacing lead shown in FIG. 1 fixed therein.

Referring now to FIG. 1 there is illustrated therein a bipolar epicardial temporary pacing lead assembly which is hereinafter simply referred to as a pacing lead and which is identified by reference numeral 10 in FIG. 1. As shown, the pacing lead 10 has a proximal end portion 12 and a distal end portion 14. Connected to the proximal end 12 is a conventional straight percutaneous needle 16 which has a sharp point 18 at the outer end and a cavity 20 at the inner end for receiving one end of a biconductor lead body 22.

The biconductor lead body 22 includes a sheath 23 and two wire conductors 24 and 26, each encased in insulation material 30 and received in the sheath 23 as shown in FIG. 2.

In the proximal end portion 12 of the lead body 22, the sheath 23 is removed and a proximal insulated wire conductor portion 32 of conductor 24 has formed thereon a terminal connector sleeve 34. Likewise, a proximal insulated wire conductor portion 33 of conductor 26 has formed thereon a terminal connector sleeve 36. The sleeves 34 and 36 are made of metal and the conductors 24 and 26 passing therethrough are mechanically and electrically connected to the respective sleeves 34 and 36 such as by a crimp 37 shown in FIG. 4 which forces an internal circular rib 38 in the area of the crimp 37 through the insulation 30 into mechanical and electrical contact with wire conductor 24 or 26.

The wire conductors 24 and 26 are received in and fixed in the cavity 20 of the needle 16. In this way, the proximal end portion 12 of the pacing lead 10 composed of the insulated wire conductors 24 and 26 with the connector sleeves 34 and 36 mounted thereon can pass through a single puncture of tissue with the straight needle 16 thereby minimizing trauma to the patient, and requiring only one puncture site.

It will be noted that the connector sleeves 34 and 36 are staggered for easy correlation of these connector sleeves 34 and 36 with electrodes 54 and 56 formed in the distal end portion 14 of the pacing lead 10 as will be described in greater detail hereinafter.

Typically the straight needle 16 can be a percutaneous needle sold by the B. G. Sulzie Co. under catalog no. 393950 SC-2 straight cutting needle.

The insulation material 30 of the lead body 22 can be a polyurethane insulation or a polytetrafluoroethylene insulation of the type sold under the trademark TEFLON.

The wire conductors 24 and 26 are preferably made of stainless steel but can also be carbon conductors or made of a conductive polymer.

The lead body 22 extends from the proximal end portion 12 to a bipolar electrode formation 57 in the distal end portion 14. At the beginning of this bipolar electrode formation 57, the sheath 23 is cut away as indicated at 58 and the insulation material 30 on the wire conductor 24 is removed over a length $L_1$ thereof which is typically 1 cm to form a first or proximal electrode-forming wire conductor portion 54 hereinafter referred to as the first electrode 59.

Meanwhile, the sheath 23 and the coating of insulation material 30 on the other wire conductor 26 is left intact as indicated by reference numeral 59 for the first length $L_1$ and a second length $L_2$ which can be equal to $L_1$ or some other suitable dimension. Then the sheath 23 is cut away as indicated at 60 and the insulation material 30 is stripped from the wire conductor 26 to form a second or distal electrode-forming wire conductor portion 56 hereinafter referred to as the second electrode. Typically the electrode 56 has a length $L_3$ of about 1 cm, equal to $L_1$ The second electrode 56 can have a length equal to the length $L_1$ of the first electrode 54 and the remainder 61 of the sheath 23 and the insulated conductors 24 and 26 can extend to the curved needle 16 as shown.

The construction of the distal end portion 14 described above is preferred since it provides a smooth, continuous distal end portion 14 of the lead 22 which is connected to a curved needle 62. Actually conductors 24 and 26 are received in and fixed in a cavity 63 in the proximal end of needle 62.

Also, in this embodiment, to isolate electrically the electrode/conductor 54 from the cut ends of conductors 24 and 26, after a distal lead body end 64 has been pulled through the epicardium and if desired through a retainer 66 (FIG. 5) and cut, the conductor 24 within the sheath portion 59 can have a break to form a gap 74 as shown in FIG. 3 having a length $L_4$ sufficient to isolate the opposed break ends of the conductor 24. Also, if desired, the conductor 26 can have a break to form a gap within the sheath portion 61.

In use, after an incision has been made to expose the heart, a surgeon sews the needle 62 into the epicardium and myocardium as shown in FIG. 3. Typically this is referred to as taking two bites with the needle 62 in the heart tissue. The "sewing" is done in such a way that electrodes 54 and 56 are positioned in the myocardium with the insulated sheath portion 56 extending therebetween to reduce or eliminate current leakage. If desired, and as shown, the sheath 23 and conductor insulation 30 can extend at least into the epicardium to reduce and hopefully eliminate leakage current.

After the electrodes 54 and 56, i.e., the bared portions of the wire conductors 24 and 26, are fixed in the position shown in FIG. 5, the end of the wire 26 connected to the curved needle 62 is cut at the position shown by a line of cut 78 as will now be described in connection with the description of FIG. 5.

The retainer 66 can be slid over the curved needle 62 and positioned adjacent the epicardium about the sheath end portion 61. This retainer 66 has a button or hub portion 80 with a bore 82 through which the wire conductor 26 can be received. A tab portion (not shown) was originally connected to the hub portion 80 and is cut off by the surgeon.

After the hub portion 80 is threaded over the needle 62 and over the sheath end portion 61, it is positioned flush against an outer surface 84 of the epicardium. Then, the wire conductor 26 is cut close to the epicardium or flush against the outer edge of the hub portion 80 along the line of cut 78 and the tab portion (not shown) is cut away from the hub portion 80.

The retainer 66 is preferably made of a medical quality silicone rubber material which may be made radioopaque if desired. The tab portion (not shown) enables one to maintain the proper position of the electrodes 54 and 56 and once both electrodes 54 and 56 are positioned properly, the button or hub shaped portion 80 is placed over the curved needle 62 and slid down the lead body end 64 to the surface 84 followed by cutting away excess lead body 22 at the end 64 with the curved needle 62 attached thereto and cutting off the tab portion (not shown).

One of the important features of the pacing lead 10 of the present invention is the provision of color coded bands which can be stamped or painted on the lead body 22. In this respect, there is provided on the sheath 23 just before the electrode 54 a first solid color band 91. Further, there is provided a second solid color band 92 on sheath portion 59 between electrodes 54 and 56. A third color band is provided on sheath end portion 61 just after electrode 56. The color bands 91–93 are black or blue black and can be defined by a short piece of thin walled shrinkable tubing slid over sheath 23 and heat shrunk in place or can be defined by a hot blue black stamping on the sheath 23.

These color bands 91–93 indicate to a physician when the first electrode 54 has been properly located in the myocardium since the bands 91 and 92 will be on either side of the first bite taken with the needle 62. Then the band 93 will indicate when the electrode 56 is in place within the myocardial tissue so that the retainer 66 can be slid onto the lead body 22 which then is cut at cut line 78.

Once the distal end portion 14 is in place with the proximal and distal electrodes 54 and 56 implanted within the myocardium as shown in FIG. 5, the proximal end portion 12 of the lead 10 will be brought out through a puncture site in the patient's skin. At this point, a silastic strain relief device (not shown) can be passed over the straight needle 16, over the proximal end portion 12 of the lead body 22 and over the terminal connector sleeves 34 and 36 and brought to a position adjacent the skin puncture site. Here a backing (not shown) on the silastic strain relief device (not shown) is removed so that a flat surface (not shown) of the device which is coated with an adhesive material, can be adhered to the skin adjacent the puncture site. Then, a suture (not shown) is tied around a hub portion (not shown) of the silastic strain relief device for fixing the lead body 22 adjacent the puncture site. In this way, pulling on the lead 10 will not dislodge the proximal end portion 14 and namely the electrodes 54 and 56 from the heart muscle tissue.

The straight needle 16 and insulated conductor portions 32 and 33 are cut away by cutting along lines of cut 100 and 102 adjacent the proximal end of each of the terminal connector sleeves 34 and 36 that are adapted to be received in mating female sockets (not shown) in a pacer (not shown).

Figure 6:
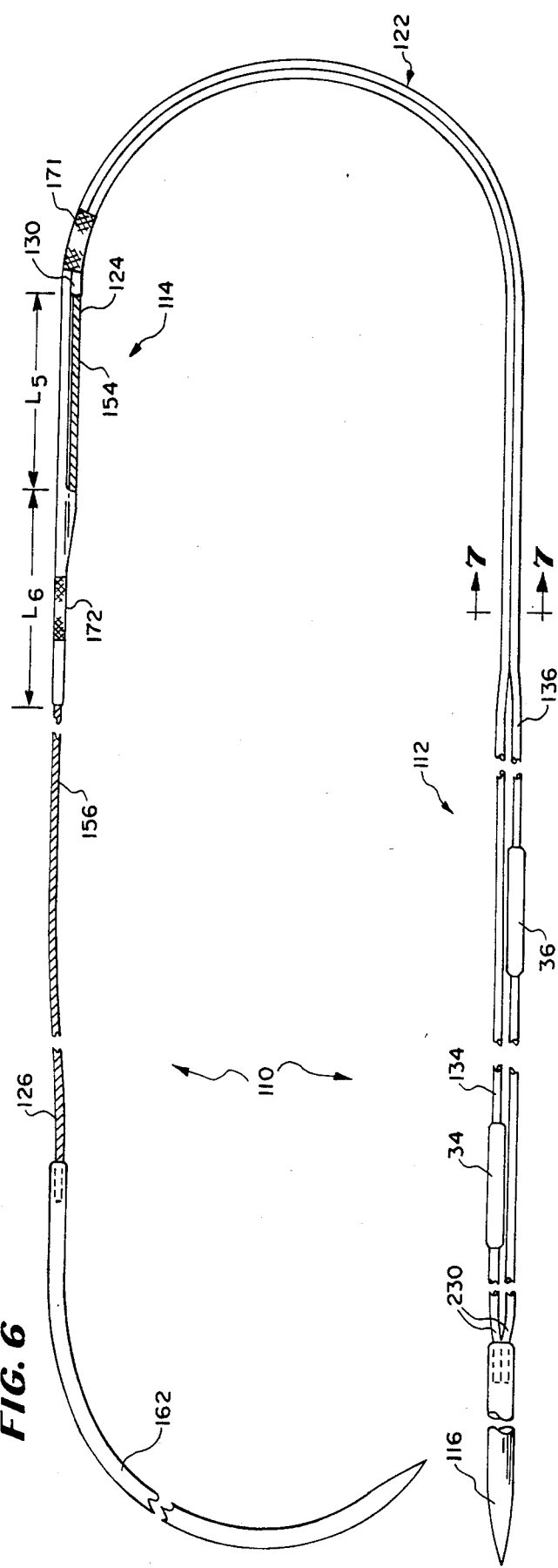
FIG. 6 is a plan view of another embodiment of the bipolar epicardial temporary pacing lead of the present invention which includes a lead body made of a zipcord type material with a curved needle at the distal end thereof and a straight needle at the proximal end thereof.

Referring now to FIG. 6, there is illustrated therein another embodiment of a bipolar epicardial temporary pacing lead which is constructed according to the teachings of the present invention and which is generally identified by reference numeral 110. The lead 110 has a proximal end 112 with a straight needle 116 identical to proximal end 12 shown in FIG. 1 but with a modified distal end portion 114 and a zip cord type lead body 122.

The zip cord type lead body 122 is very similar to a common lamp cord. In this respect and as shown in FIG. 7, the lead body 122 includes two conductors 124 and 126 encased in an insulation material 130 to form a figure eight about the conductors 124 and 126 with an area of reduced thickness 131 between the conductors 124 and 126 so as to form insulated conductor portions 134 and 136.

One suitable biconductor insulated zip cord is of the type made by the Cooner Wire Company and comprises an insulation sold under the trademark PELETHANE 55D which is extruded onto 33 gauge stranded stainless steel wire in a zip cord fashion.

Where the insulation material 130 is soft and has a low tensile strength, a small cut can be made in the area 131 in the zip cord 122 in proximal end portion 112 and the conductor portions 134 and 136 can be easily pulled apart. And, where the insulation material 130 is relatively hard with a high tensile strength, the conductor portions 134 and 136 are typically pre-cut apart at the factory before the lead 110 is packaged and shipped.

The zip cord 122 extends from the proximal end 112 to a bipolar electrode formation 152 in the distal end portion 114. At the beginning of this bipolar electrode formation, the insulation material 130 on the wire conductor 124 is removed over a length $L_5$ thereof, which is about 1 cm, to form a first or proximal electrode 154.

Meanwhile, the coating of insulation material 130 on the other wire conductor 126 is left intact, as indicated by the insulated conductor portion 158, for the first length $L_5$ and a second length $L_6$ which can be equal to $L_4$ or some other suitable dimension. Then the insulation material 130 is stripped from the wire conductor 126 to form the second or distal electrode 156. As shown, this bared wire conductor 126 extends from the electrode forming portion 156 to the proximal end of a curved needle 162 where it is fixed to the needle 162.

A deposit of epoxy 164 can be placed over an end 166 of the first electrode 154 for securing the end 166 to the insulation material 158 covering the wire conductor 126 in the formation 152. This deposit 164 provides a smooth transition from the first electrode 154 to the insulated wire conductor portion 158 which then extends to the bared electrode defining portion 156 of the bare conductor 126 connected to the curved needle 162.

In using the bipolar epicardial temporary fixation lead 10 or 110, a surgeon will grasp the needle 62 or 162 and pass it through the epicardium at the intended cardiac pacing sites on the outside of the atrium or ventricle. Two bites of the needle 62 or 162 are taken, one for implanting the proximal electrode 54 or 154 and one for implanting the distal electrode 56 or 156. Then, the curved needle 62 or 162 can be passed through a hub or button portion 80 of a retainer 66 while grasping a ribbed tab portion thereof (not shown) between the thumb and forefinger. Next, the retainer 66 is slid over the needle 62 or 162 and the conductor or conductors connected thereto until it fits snugly against the outer surface 84 of the epicardium as shown in FIG. 5. Then, the tab portion (not shown) is cut away from the retainer 66.

Next the curved needle 62 or 162 and excess lead body 22 or 122 is cut flush with the exterior top surface of the hub or button portion 80 of the retainer 66.

At this point a cardiac lead extension cable from the cathodic (−) and anodic (+) connectors of an external pacer are brought into contact with terminal connector sleeves 34 and 36. Then, the surgeon will verify the acceptable positioning of the electrodes 54 or 154 and 56 or 156 by noting the location of the color bands 91–93 on lead 10, or color bands 171 and 172 on lead 114, and by testing stimulation threshold and sensitivity. The output and sensitivity settings of the external pacer are then set to allow for an adequate safety margin. If repositioning is required, the distal end portion 14 or 114 of the lead 10 or 110 is pulled out of the heart and discarded. Implantation is then repeated with a new lead 10 or 110 at another site.

Then at a site away from the main incision, the straight needle 16 or 116 is pushed through the chest wall forming a puncture site and the lead 10 or 110 is drawn through the puncture site in the skin with some excess lead left inside the chest cavity to allow for cardiac contractions and patient movement. One must be careful at this point to arrange the excess lead in a manner that precludes the possibility of a knot forming in the lead 10, 110 upon removal from the chest cavity. Then the straight needle 16 or 116 can be passed through a strain relief device (not shown) and a split covering on an adhesive side of the strain relief device can be removed from a disk portion thereof and the disk portion can be secured to the skin about the exit puncture site. Then a suture can be tied firmly around an annular groove on a hub portion of the strain relief device to fix the lead 10 or 110 in place.

An identification tag having a correct position code such as A=atrium, V=ventricle or G=ground is passed over the appropriate connector sleeves 34 and 36. Next the nonconductive straight needle 16 or 116 is cut away by cutting the conductor portions 32 or 134 and 33 or 136 adjacent the proximal end of the terminal connector sleeves 34 and 36.

Now one terminal connector sleeve 34 is connected to the cathodic (−) connector of the external pacer and the other terminal connector sleeve 36 is connected to the anodic (+) connector of the external pacer.

When it is desired to remove the implanted bipolar epicardial temporary pacing lead 10 or 110, the strain relief device is peeled off the skin and the lead 10 or 110 is pulled out where it exits the skin through the puncture site. The retainer hub or button portion 80 or retainer 66 will slip off the distal end portion 14 or 114 of the lead 10 or 110 and remain in place on the surface of the heart.

From the foregoing description, it will be apparent that the bipolar epicardial temporary pacing leads 10 or 110 of the present invention provide a number of advantages, some of which have been described above and others of which are inherent in the invention. In particular, with the pacing lead 10 or 110, a minimum of exit sites is required and the patient is subjected to a minimum of trauma.

Also the marking of the leads with the bands 91–93 or 171–172 in the distal end portion 14 or 114, thereof provide for easy identification and location of the proximal electrode 54 or 154, and the distal electrode 56 or 156.

Most significantly, the pacing leads 10 and 110 of the present invention provide temporary bipolar epicardial pacing leads which heretofore have not been available.

It will also be apparent to those skilled in the art that modifications can be made to the bipolar epicardial temporary pacing lead 10 or 110 of the present invention without departing from the teachings of the present invention. Accordingly, the scope of the invention is only to be limited as necessitated by the accompanying claims.

I claim:

1. A bipolar temporary pacing lead comprising a lead body having a proximal end portion and a distal end portion and including first and second spaced apart wire conductors each encased in insulating material to form insulated wire conductors, a curved needle, at least one of said first and second wire conductors in said lead body distal end portion being connected to said curved needle, a straight needle, the proximal end portion of said lead body being connected to said straight needle, and said distal end portion of said lead body having insulation removed from portions of said respective first and second conductors thereby to form in said lead body distal end portion a first electrode-forming bare wire conductor portion and a second electrode-forming bare wire conductor portion.

2. The pacing lead of claim 1 wherein said second wire conductor is fixed to said curved needle.

3. The pacing lead of claim 2 wherein said proximal end portion of said lead body has a first terminal connector sleeve fixed around said first insulated wire conductor and electrically and mechanically connected to said first wire conductor therein and a second terminal connector sleeve spaced from said first terminal sleeve connector and fixed around said second insulated wire conductor and electrically and mechanically connected to said second wire conductor therein.

4. The pacing lead of claim 3 wherein said first terminal sleeve is situated closer to said straight needle than said second terminal sleeve.

5. The pacing lead of claim 1 wherein said first electrode-forming wire conductor portion is proximal relative to and spaced from said second electrode forming bare wire conductor portion such that said first electrode is a proximal electrode and said second electrode is a distal electrode.

6. The pacing lead of claim 5 wherein said first wire conductor has insulation removed therefrom in said lead body distal end portion to form said proximal electrode while said second insulated wire conductor portion remains insulated for the length of said proximal electrode and beyond a suitable distance to a point where said second wire conductor has insulation removed therefrom to form said distal electrode.

7. The pacing lead of claim 6 wherein said distal end of said first insulated wire conductor portion is cut at the distal end of said proximal electrode and is fixed thereat to said second insulated wire conductor portion.

8. The pacing lead of claim 7 wherein said distal electrode-forming second wire conductor portion extends all the way to said curved needle.

9. The pacing lead of claim 7 wherein a portion of said second wire conductor between said curved needle and said distal electrode forming wire conductor portion is covered with insulation.

10. The pacing lead of claim 6 wherein said second insulated wire conductor portion remains insulated beyond said proximal electrode a length equal to the length of said proximal electrode.

11. The pacing lead of claim 10 wherein the length of said proximal electrode, the length of said distal electrode and the length of said second insulated wire conductor portion therebetween are the same.

12. The pacing lead of claim 11 wherein said three lengths are all about one centimeter.

13. The pacing lead of claim 5 wherein a first terminal connector sleeve is fixed around said first insulated wire conductor portion and electrically and mechanically connected to said first wire conductor therein and a second terminal connector sleeve spaced from said first terminal sleeve is fixed around said second insulated wire conductor portion and electrically and mechanically connected to said second wire conductor therein in the proximal end portion of said lead body.

14. The pacing lead of claim 13 wherein said first terminal sleeve is situated closer to said straight needle than said second terminal sleeve.

15. The pacing lead of claim 5 wherein said lead body in the area between said wire-conductor-forming electrodes has a color coded band thereon.

16. The pacing lead of claim 5 wherein said lead body in the area just before said proximal electrode has a color coded band thereon.

17. The pacing lead of claim 5 wherein said lead body in the area between said distal wire-conductor-forming electrode and said curved needle has a color coded band thereon.

18. The pacing lead of claim 1 wherein said second insulated wire conductor portion only has insulation removed for the chosen length of said distal electrode formed by the uninsulated second wire conductor portion and the remainder thereof extending to said curved needle remains insulated.

19. The pacing lead of claim 1 wherein the distal end portions of the wire conductors in said lead body are covered with insulation.

20. The pacing lead of claim 1 wherein said distal ends of said first and second insulated wire conductor portions adjacent each other are fixed to the proximal end of said curved needle.

21. The pacing lead of claim 1 wherein said lead body includes a sheath which extends from said curved needle to a point spaced from said straight needle and portions of said sheath are cut away in the area of said uninsulated electrode forming wire conductor portions to expose same.

22. The pacing lead of claim 21 wherein the lengths of said proximal and distal electrode-forming wire conductor portions are such that when they are threaded into the mycocardium through the epicardium, the insulated wire conductor portion at each end of each electrode formed by the uninsulated portion thereof extends into at least the epicardium to minimize leakage current through body fluids between said proximal and distal electrodes.

23. The pacing lead of claim 1 wherein said wire conductors are made of stainless steel or other metal alloy.

24. The pacing lead of claim 1 wherein said wire conductors are each made of wound strands of stainless steel or other metal alloy.

25. The pacing lead of claim 1 wherein said wire conductors are made of graphite carbon.

26. The pacing lead of claim 1 wherein said wire conductors are made of a conductive polymer.

27. A method for implanting a bipolar temporary pacing lead comprising a lead body having a proximal end portion and a distal end portion and including first and second spaced apart wire conductors each encased in insulating material to form insulated wire conductors, a curved needle, at least one of said first and second wire conductors in said lead body distal end portion being connected to said curved needle, a straight needle, the proximal end portion of said lead body being connected to said straight needle, and said distal end portion of said lead body having insulation removed from portions of said respective first and second conductors thereby to form in said lead body distal end portion a first electrode forming, bare wire conductor portion and a second electrode forming bare wire conductor portion, said first electrode forming wire conductor portion being proximal to and spaced from said second electrode forming bare wire conductor portion such that said first electrode is a proximal electrode and said second electrode is a distal electrode, a first terminal connector sleeve being fixed around said first insulated wire conductor portion and electrically and mechanically connected to said first wire conductor therein and a second terminal connector sleeve spaced from said first terminal sleeve connector is fixed around said second insulated wire conductor portion and electrically and mechanically connected to said second wire conductor therein in the proximal end portion of said lead body in an exposed heart, said method including the steps of:

taking a first bite with said curved needle through the epicardium to place said proximal electrode in the myo- cardium;

taking a second bite with said curved needle through the epicardium to place said distal electrode in the myocardium spaced from said proximal electrode;

temporarily connecting a pulse generator to said terminal connector sleeves and electrically checking the functioning of the electrodes and if they function properly, disconnecting the pulse generator;

cutting off wire conductor end portion(s) close to the epicardium;

passing the straight needle through a puncture site in a patent's chest wall;

leaving a portion of the lead body in the chest cavity to compensate for heart contractions and body movement;

placing appropriate identification tags over the connector sleeves;

cutting the respective wire conductor portions flush with the proximal ends of the respective terminal connector sleeves; and inserting the terminal connector sleeves in respective female sockets therefor in a pacer.

28. A bipolar epicardial temporary pacing lead comprising a lead body having a proximal end and a distal end and including first and second spaced apart wire conductors each encased in insulating material so as to form first and second insulated wire conductor portions and a sheath in which said insulated wire conductor portions are received, a straight needle connected to the proximal end of said lead body, a curved needle, the distal ends of said first and second wire conductors being connected to said curved needle, and said distal end portion of said lead body having portions of said sheath removed therefrom and adjacent portions of said conductor insulation removed from spaced apart portions of said respective first and second conductors thereby to form in said lead body distal end portion a proximal first electrode-forming wire conductor portion and a distal or second electrode-forming wire conductor portion.

* * * * *